(12) United States Patent
Feucht et al.

(10) Patent No.: US 9,968,091 B2
(45) Date of Patent: May 15, 2018

(54) SELECTIVE HERBICIDES BASED ON SUBSTITUTED THIEN-3-YL-SULPHONYLAMINO(THIO)CARBONYLTRIAZOLIN(THI)ONES AND SAFENERS

(71) Applicant: Bayer CropScience AG, Monheim (DE)

(72) Inventors: Dieter Feucht, Monheim (DE); Peter Dahmen, Neuss (DE); Mark Wilhelm Drewes, Langenfeld (DE); Rolf Pontzen, Leichlingen (DE); Ernst Rudolf F. Gesing, Erkrath (DE); Hans-Georg Schwarz, Langenfeld (DE); Klaus-Helmut Müller, Duesseldorf (DE)

(73) Assignee: BAYER CROPSCIENCE AG, Monheim (DE)

( * ) Notice: Subject to any disclaimer, the term of this patent is extended or adjusted under 35 U.S.C. 154(b) by 639 days.

(21) Appl. No.: 13/873,656

(22) Filed: Apr. 30, 2013

(65) Prior Publication Data
US 2013/0237418 A1 Sep. 12, 2013

Related U.S. Application Data

(63) Continuation of application No. 10/489,092, filed as application No. PCT/EP02/10104 on Sep. 10, 2002, now abandoned.

(30) Foreign Application Priority Data

Sep. 21, 2001 (DE) .................................. 101 46 590

(51) Int. Cl.
*A01N 47/38* (2006.01)
*A01N 25/32* (2006.01)
*A01N 43/653* (2006.01)

(52) U.S. Cl.
CPC .............. *A01N 47/38* (2013.01); *A01N 25/32* (2013.01); *A01N 43/653* (2013.01)

(58) Field of Classification Search
CPC ....... A01N 47/38; A01N 43/653; A01N 25/32
See application file for complete search history.

(56) References Cited

U.S. PATENT DOCUMENTS

| | | | |
|---|---|---|---|
| 4,021,224 A | 5/1977 | Pallos et al. |
| 4,137,070 A | 1/1979 | Pallos et al. |
| 4,186,130 A | 1/1980 | Teach |
| 4,243,811 A | 1/1981 | Teach |
| 4,269,618 A | 5/1981 | Pallos et al. |
| 4,415,352 A | 11/1983 | Pallos et al. |
| 4,415,353 A | 11/1983 | Pallos et al. |
| 4,623,727 A | 11/1986 | Hubele |
| 4,639,266 A | 1/1987 | Heubach et al. |
| 4,708,735 A | 11/1987 | Pallos et al. |
| 4,758,264 A | 7/1988 | Hubele |
| 4,785,105 A | 11/1988 | Hubele |
| 4,785,106 A | 11/1988 | Hubele |
| 4,822,884 A | 4/1989 | Hubele |
| 4,851,033 A | 7/1989 | Hubele |
| 4,881,966 A | 11/1989 | Nyffeler et al. |
| 4,891,057 A | 1/1990 | Sohn et al. |
| 4,902,340 A | 2/1990 | Hubele |
| 4,964,893 A | 10/1990 | Brannigan et al. |
| 4,971,618 A | 11/1990 | Pallos et al. |
| 5,023,333 A | 6/1991 | Hubele |
| 5,045,107 A | 9/1991 | Hubele |
| 5,061,311 A | 10/1991 | Findeisen et al. |
| 5,082,949 A | 1/1992 | Sohn et al. |
| 5,102,445 A | 4/1992 | Hubele |
| 5,149,356 A | 9/1992 | Muller et al. |
| 5,166,356 A | 11/1992 | Findeisen et al. |
| 5,262,389 A | 11/1993 | Findeisen et al. |
| 5,276,162 A | 1/1994 | Muller et al. |
| 5,314,863 A | 5/1994 | Loher et al. |
| 5,380,852 A | 1/1995 | Schutze et al. |
| 5,380,863 A | 1/1995 | Muller et al. |

(Continued)

FOREIGN PATENT DOCUMENTS

EP 0346620 A1 12/1989
WO 0105788 A1 1/2001

*Primary Examiner* — Kortney L Klinkel
(74) *Attorney, Agent, or Firm* — McBee Moore Woodward & Vanik IP, LLC; Susan McBee; David Woodward

(57) ABSTRACT

The invention relates to selective herbicidal compositions that comprise an effective amount of an active compound combination comprising
(a) one or more compounds of the formula (I)

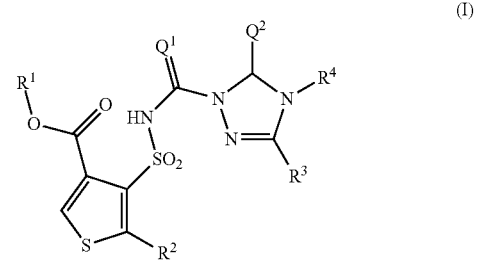

(I)

in which $Q^1$, $Q^2$, $R^1$, $R^2$, $R^3$ and $R^4$ are as defined in the disclosure—and salts of the compounds of the formula (I)— and
(b) at least one of the crop-plant-compatibility-improving compounds listed in the disclosure.
The invention further relates to the use of these compositions for controlling undesirable vegetation and to a process for preparing the compositions according to the invention.

10 Claims, No Drawings

(56) References Cited

U.S. PATENT DOCUMENTS

| | | |
|---|---|---|
| 5,401,700 A | 3/1995 | Sohn et al. |
| 5,407,897 A | 4/1995 | Cary et al. |
| 5,516,750 A | 5/1996 | Willms et al. |
| 5,516,918 A | 5/1996 | Cary et al. |
| 5,523,409 A | 6/1996 | Findeisen et al. |
| 5,552,369 A | 9/1996 | Findeisen et al. |
| 5,599,944 A | 2/1997 | Muller et al. |
| 5,654,438 A | 8/1997 | Findeisen et al. |
| 5,696,050 A | 12/1997 | Cary et al. |
| 5,700,758 A | 12/1997 | Rosch et al. |
| 5,703,008 A | 12/1997 | Rosch et al. |
| 5,739,076 A | 4/1998 | Huybrechts et al. |
| 5,750,718 A | 5/1998 | Muller et al. |
| 5,945,541 A | 8/1999 | Sohn et al. |
| 6,121,204 A | 9/2000 | Muller et al. |
| 6,162,762 A | 12/2000 | Cornes et al. |
| 6,235,680 B1 | 5/2001 | Ziemer et al. |
| 6,251,827 B1 | 6/2001 | Ziemer et al. |
| 6,482,947 B1 | 11/2002 | Holdgrun et al. |
| 6,511,940 B1 | 1/2003 | Ziemer et al. |
| 6,964,939 B1 | 11/2005 | Gesing et al. |
| 7,642,221 B2 | 1/2010 | Gesing et al. |
| 7,858,805 B2 | 12/2010 | Gesing et al. |
| 2003/0171220 A1 | 9/2003 | Ziemer et al. |
| 2005/0130843 A1 | 6/2005 | Gesing et al. |
| 2010/0056798 A1 | 3/2010 | Gesing et al. |

SELECTIVE HERBICIDES BASED ON SUBSTITUTED THIEN-3-YL-SULPHONYLAMINO(THIO)CARBONYLTRIAZOLIN(THI)ONES AND SAFENERS

CROSS REFERENCE TO RELATED APPLICATIONS

This application is a Continuation of U.S. application Ser. No. 10/489,092, filed Sep. 7, 2004, which is a §371 National Stage Application of PCT/EP2002/010104, filed Sep. 10, 2002, which claims priority to German Application No. 101 46 590.4, filed Sep. 21, 2001, the content of all of which are incorporated herein by reference in their entireties.

BACKGROUND

Field of the Invention

The invention relates to novel selective herbicidal active compound combinations which comprise substituted thien-3-ylsulphonylamino(thio)carbonyltriazolin(ethi)ones and at least one compound which improves crop plant compatibility and which can be used with particularly good results for the selective control of weeds in various crops of useful plants.

Description of Related Art

Substituted thien-3-ylsulphonylamino(thio)carbonyltriazoline(ethi)ones are already known as effective herbicides (cf. WO-A-01/05788). However, the activity of these compounds and/or their compatibility with crop plants are not entirely satisfactory under all conditions.

SUMMARY

Surprisingly, it has now been found that certain substituted thien-3-ylsulphonylamino(thio)carbonyltriazolin(ethi)ones, when used together with the crop-plant-compatibility-improving compounds (safeners/antidotes) described below, prevent damage to crop plants extremely well and can be used particularly advantageously as broad-spectrum combination preparations for the selective control of weeds in crops of useful plants, such as, for example, in cereals and maize.

The invention provides selective herbicidal compositions, characterized by an effective amount of an active compound combination comprising
(a) substituted thien-3-ylsulphonylamino(thio)carbonyltriazolin(ethi)ones of the formula (I)

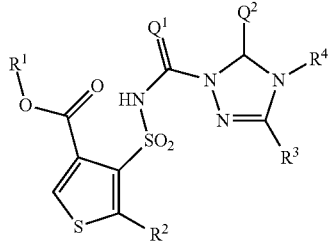

in which
$Q^1$ represents O (oxygen) or S (sulphur),
$Q^2$ represents O (oxygen) or S (sulphur),
$R^1$ represents optionally cyano-, halogen- or $C_1$-$C_4$-alkoxy-substituted alkyl having 1 to 6 carbon atoms, represents in each case optionally cyano- or halogen-substituted alkenyl or alkynyl having in each case 2 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, represents in each case optionally nitro-, cyano-, halogen-, $C_1$-$C_4$-alkyl- or $C_1$-$C_4$-alkoxy-substituted aryl or arylalkyl having in each case 6 or 10 carbon atoms in the aryl group and, if appropriate, 1 to 4 carbon atoms in the alkyl moiety, or represents in each case optionally nitro-, cyano-, halogen-, $C_1$-$C_4$-alkyl- or $C_1$-$C_4$-alkoxy-substituted heterocyclyl or heterocyclylalkyl having in each case up to 6 carbon atoms and additionally 1 to 4 nitrogen atoms and/or 1 or 2 oxygen or sulphur atoms in the heterocyclyl group and, if appropriate, 1 to 4 carbon atoms in the alkyl moiety, $R^2$ represents hydrogen, cyano, nitro, halogen, represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 6 carbon atoms in the alkyl group, or represents in each case optionally cyano- or halogen-substituted alkenyl, alkynyl, alkenyloxy or alkynyloxy having in each case 2 to 6 carbon atoms in the alkenyl or alkynyl group, $R^3$ represents hydrogen, hydroxyl, mercapto, amino, cyano, fluorine, chlorine, bromine, iodine, represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkynyl having in each case 2 to 6 carbon atoms, represents in each case optionally fluorine-, chlorine-, cyano-, $C_1$-$C_4$-alkoxy- or $C_1$-$C_4$-alkoxy-carbonyl-substituted alkoxy, alkylthio, alkylamino or alkylcarbonylamino having in each case 1 to 6 carbon atoms in the alkyl group, represents alkenyloxy, alkynyloxy, alkenylthio, alkynylthio, alkenylamino or alkynylamino having in each case 3 to 6 carbon atoms in the alkenyl or alkynyl group, represents dialkylamino having in each case 1 to 4 carbon atoms in the alkyl groups, represents in each case optionally methyl- and/or ethyl-substituted aziridino, pyrrolidino, piperidino and/or morpholino, represents in each case optionally fluorine-, chlorine-, bromine-, cyano- and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkyl-alkylthio or cycloalkylalkylamino having in each case 3 to 6 carbon atoms in the cycloalkyl or cycloalkenyl group and, if appropriate, 1 to 4 carbon atoms in the alkyl moiety, or represents in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, aryl-thio, arylalkylthio, arylamino or arylalkylamino having in each case 6 or 10 carbon atoms in the aryl group and, if appropriate, 1 to 4 carbon atoms in the alkyl moiety, $R^4$ represents hydrogen, hydroxyl, amino, cyano, represents $C_2$-$C_{10}$-alkylidene-amino, represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkynyl having in each case 2 to 6 carbon atoms, represents in each case optionally fluorine-, chlorine-, bromine-, cyano-, $C_1$-$C_4$-alkoxy- or $C_1$-$C_4$-alkoxy-carbonyl-substituted alkoxy, alkylamino or alkyl-carbonylamino having in each case 1 to 6 carbon atoms in the alkyl group, represents alkenyloxy having 3 to 6 carbon atoms, represents dialkylamino having in each case 1 to 4 carbon atoms in the alkyl groups, represents in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and, if appropriate, 1 to 4 carbon atoms in the alkyl moiety, or represents in each case optionally fluorine-, chlorine-, bromine-, cyano-nitro-, $C_1$-$C_4$-alkyl-, trifluoromethyl- and/or $C_1$-$C_4$-alkoxy-substituted aryl or arylalkyl having in each case 6 or 10 carbon atoms in the aryl group and, if appropriate, 1 to 4 carbon atoms in the alkyl moiety, or $R^3$ and $R^4$ together represent optionally branched alkanediyl having 3 to 6 carbon atoms, —and salts of the compounds of the formula (I)—

("active compounds of group 1")

and (b) at least one compound which improves crop plant compatibility, from the group of compounds below:

4-dichloroacetyl-1-oxa-4-aza-spiro[4.5]-decane (AD-67, MON-4660), 1-dichloroacetyl-hexahydro-3,3,8a-trimethylpyrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl—cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyanomethoximino)-phenylacetonitrile (cyometrinil), 2,4-dichloro-phenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamiba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazole-ethyl—cf. also related compounds in EP-A-174562 and EP-A-346620), phenyl-methyl 2-chloro-4-trifluoromethyl-thiazole-5-carboxylate (flurazole), 4-chloro-N-(1,3-dioxolan-2-yl-methoxy)-α-trifluoroacetophenone oximne (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)-ethyl-3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-yl-methoximino)-phenylacetonitrile (oxabetinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chloro-phenoxy)-butyric acid, diphenylmethoxyacetic acid, methyl diphenylmethoxyacetate (MON-7400, cf. U.S. Pat. No. 4,964,893), ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-11H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf. also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinolin-8-oxy-acetate, ethyl 5-chloro-quinolin-8-oxy-acetate, allyl 5-chloro-quinolin-8-oxy-acetate, 2-oxo-prop-1-yl 5-chloro-quinolin-8-oxy-acetate, diethyl 5-chloro-quinolin-8-oxy-malonate, diallyl 5-chloro-quinolin-8-oxy-malonate, diethyl 5-chloro-quinolin-8-oxy-malonate (cf. also related compounds in EP-A-582 198), 4-carboxy-chroman-4-yl-acetic acid (AC-304415, cf. EP-A-613618), 4-chloro-phenoxyacetic acid, 3,3'-dimethyl-4-methoxy-benzophenone, 1-bromo-4-chloromethylsulphonyl-benzene, 1-[4-(N-2-methoxybenzoylsulphamoyl)-phenyl]-3-methyl-urea (alias N-(2-methoxybenzoyl)-4-[(methylamino-carbonyl)-amino]-benzenesulphonamide), 1-[4-(N-2-methoxybenzoylsulphamoyl)-phenyl]-3,3-dimethyl-urea, 1-[4-(N-4,5-dimethylbenzoylsulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropyl-aminocarbonyl)-benzenesulphonamide, and/or the following compounds of the formula (IIa)

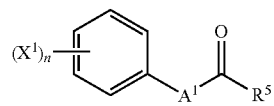

(IIa)

or the formula (IIb)

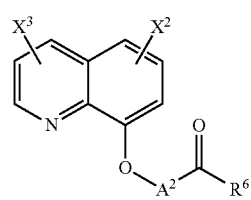

(IIb)

or the formula (IIc)

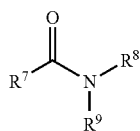

where n represents a number between 0 and 5, $A^1$ represents one of the divalent heterocyclic groupings shown below,

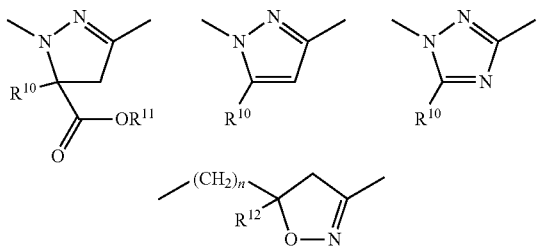

$A^2$ represents optionally $C_1$-$C_4$-alkyl- and/or $C_1$-$C_4$-alkoxy-carbonyl-substituted alkanediyl having 1 or 2 carbon atoms, $R^5$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)-amino, $R^6$ represents hydroxyl, mercapto, amino, in each case optionally $C_1$-$C_4$-alkyl, $C_1$-$C_4$-alkoxy or $C_2$-$C_4$-alkenoxy-substituted $C_1$-$C_6$-alkoxy, $C_2$-$C_6$-alkenoxy, $C_1$-$C_6$-alkylthio, $C_1$-$C_6$-alkylamino or di-($C_1$-$C_4$-alkyl)-amino, $R^7$ represents in each case optionally fluorine-, chlorine- and/or bromine-substituted $C_1$-$C_4$-alkyl, $R^8$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^9$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or together with $R^8$ represents $C_3$-$C_6$-alkanediyl or $C_2$-$C_5$-oxaalkanediyl, each of which is optionally substituted by $C_1$-$C_4$-alkyl, phenyl, furyl, a fused-on benzene ring or by two substituents which together with the C atom to which they are attached form a 5- or 6-membered carbocycle, $R^{10}$ represents hydrogen, cyano, halogen, or represents in each case optionally fluorine, chlorine- and/or bromine-substituted $C_1$-$C_4$-alkyl, $C_3$-$C_6$-cycloalkyl or phenyl, $R^{11}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{12}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, where $X^1$ is preferably found at the (2) and (4) positions, $X^2$ is preferably found at the (5) position and $X^3$ is found at the (2) position, and/or the following compounds of the formula (IId)

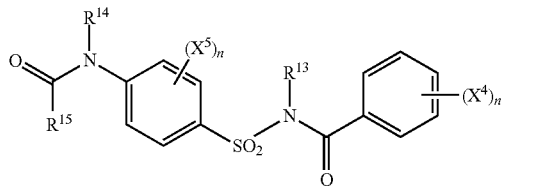

or the formula (IIe)

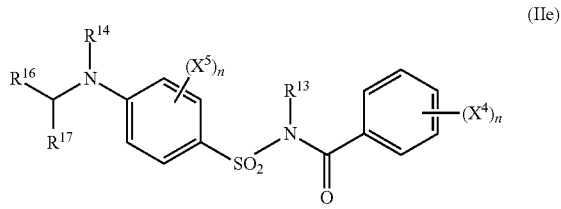

where n again represents a number between 0 and 5, $R^{13}$ represents hydrogen or $C_1$-$C_4$-alkyl, $R^{14}$ represents hydrogen or $C_1$-$C_4$-alkyl, $R^{15}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{16}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{17}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano, halogen-, $C_1$-$C_4$-alkyl-, $C_1$-$C_4$-halogenoalkyl-, $C_1$-$C_4$-alkoxy- or $C_1$-$C_4$-halogenoalkoxy-substituted phenyl, or together with $R^{16}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl. hydroxyl, amino, halogen, $C_1$-$C_4$-alkyl, $C_1$-$C_4$-haloalkyl, $C_1$-$C_4$-alkoxy or $C_1$-$C_4$-haloalkoxy. and $X^5$ represents nitro, cyano, carboxyl. carbamoyl. formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, where $X^4$ is preferably located in position (2) and/or (5)

("active compounds of group 2").

DETAILED DESCRIPTION OF A PREFERRED EMBODIMENT

In the definitions, the hydrocarbon chains, such as in alkyl or alkanediyl, are in each case straight-chain or branched—including in combination with hetero atoms, such as in alkoxy.

Preferred meanings of the groups listed above in connection with the formula (I) are defined below.

$Q^1$ preferably represents O (oxygen) or S (sulphur).

$Q^2$ preferably represents O (oxygen) or S (sulphur).

$R^1$ preferably represents in each case optionally cyano-, fluorine-, chlorine-, methoxy- or ethoxy-substituted methyl, ethyl, n- or i-propyl, n-, i-, s- or tbutyl, represents in each case optionally cyano-, fluorine- or chlorine-substituted propenyl, butenyl, propynyl or butynyl, represents in each case optionally cyano-. fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl, phenylmethyl or phenyl-ethyl, or represents in each case optionally cyano-, fluorine-, chlorine-, bromine-, methyl-, ethyl-, n- or i-propyl-, methoxy-, ethoxy-, n- or i-propoxy-substituted heterocyclyl or heterocyclylmethyl, where the heterocyclyl group is in each case selected from the group consisting of oxetanyl, thietanyl, furyl, tetrahydrofuryl, thienyl, tetrahydrothienyl.

$R^2$ represents hydrogen, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methyl-sulphonyl or ethylsulphonyl, or represents in each case optionally cyano-, fluorine- or chlorine-substituted propenyl, butenyl, propynyl, butynyl, propenyloxy, butenyloxy, propynyloxy or butynyloxy.

$R^3$ represents hydrogen, hydroxyl, mercapto, amino, cyano, fluorine, chlorine, bromine, represents in each case optionally fluorine-, chlorine-, cyano-, methoxy-, ethoxy-, n- or i-propoxy-, acetyl-, propionyl-, n- or i-butyroyl, methoxycarbonyl-, ethoxycarbonyl-, n- or i-propoxycarbonyl-substituted methyl, ethyl, n- or i-propyl, n-, i-, s- or t-butyl, represents in each case optionally fluorine-, chlorine- and/or bromine-substituted ethenyl, propenyl, butenyl, ethynyl, propynyl or butynyl, represents in each case optionally fluorine-, chlorine-, cyano-, methoxy-, ethoxy-, n- or i-propoxy-, methoxycarbonyl-, ethoxycarbonyl-, n- or i-propoxycarbonyl-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, acetylamino or propionylamino, represents propenyloxy, butenyloxy, ethynyloxy, propynyloxy, butynyloxy, propenylthio, butenylthio, propynylthio, butynylthio, propenylamino, butenylamino, propynylamino or butynylamino, represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclo-butylmethylamino, cyclopentylmethylamino or cyclohexylmethylamino, or represents in each case optionally fluorine-, chlorine-, bromine-, methyl-, trifluoromethyl-, methoxy- or methoxycarbonyl-substituted phenyl, benzyl, phenoxy, benzyloxy, phenylthio, benzylthio, phenylamino or benzylamino.

$R^4$ preferably represents hydrogen, hydroxyl, amino, represents in each case optionally fluorine-, chlorine-, cyano-, methoxy- or ethoxy-substituted methyl, ethyl, n- or i-propyl, n-, i-, s- or t-butyl, represents in each case optionally fluorine, chlorine, and/or bromine-substituted ethenyl, propenyl, butenyl, propynyl or butynyl, represents in each case optionally fluorine-, chlorine-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, represents propenyloxy or butenyloxy, represents dimethylamino or diethylamino, represents in each case optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally fluorine-, chlorine-, methyl-, trifluoromethyl- and/or methoxy-substituted phenyl or benzyl.

$R^3$ and $R^4$ together preferably represent trimethylene (propane-1,3-diyl), tetra-methylene (butane-1,4-diyl) or pentamethylene (pentane-1,5-diyl).

$Q^1$ particularly preferably represents O (oxygen).

$Q^2$ particularly preferably represents O (oxygen).

$R^1$ particularly preferably represents in each case optionally fluorine-, chlorine-, methoxy- or ethoxy-substituted methyl, ethyl, n- or i-propyl.

$R^2$ particularly preferably represents fluorine, chlorine, bromine or represents in each case optionally fluorine-, chlorine-, methoxy- or ethoxy-substituted methyl, ethyl, n- or i-propyl.

$R^3$ particularly preferably represents hydrogen, chlorine, bromine, represents in each case optionally fluorine-, chlorine-, methoxy-, ethoxy-, n- or i-propoxy-substituted methyl, ethyl, n- or i-propyl, represents in each case optionally fluorine- or chlorine-substituted ethenyl, propenyl, butenyl, propynyl or butynyl, represents in each case optionally fluorine-, chlorine-, methoxy-, ethoxy-, n- or i-propoxy-substituted methoxy, ethoxy, n- or i-propoxy, methylthio, ethylthio, n- or i-propylthio, methylamino, ethylamino, n- or i-propylamino, represents propenyloxy, propynyloxy, propenylthio, propynylthio, propenylamino or propynylamino, represents dimethylamino or diethylamino, represents in each case optionally fluorine-, chlorine- or methyl-substituted cyclopropyl, cyclopropyloxy, cyclopropylmethyl or cyclopropylmethoxy.

$R^4$ particularly preferably represents in each case optionally fluorine-, chlorine-, methoxy- or ethoxy-substituted methyl, ethyl, n- or i-propyl, represents in each case optionally fluorine- or chlorine-substituted ethenyl, propenyl or propynyl, represents in each case optionally fluorine-, chlorine-, methoxy- or ethoxy-substituted methoxy, ethoxy, n- or i-propoxy, represents methylamino, or represents cyclopropyl.

Most preferably, $R^1$ and $R^2$ represent methyl, ethyl, n- or i-propyl.

Preferred active compound components of group 1 are in particular also the sodium, potassium, magnesium, calcium, ammonium, $C_1$-$C_4$-alkylammonium-, di-($C_1$-$C_4$-alkyl)ammonium-, tri-($C_1$-$C_4$-alkyl)ammonium, tetra-($C_1$-$C_4$-alkyl)ammonium, tri-($C_1$-$C_4$-alkyl)sulphonium-, $C_5$- or $C_6$-cycloalkylammonium and di-($C_1$-$C_2$-alkyl)-benzylammonium salts of compounds of the formula (I) in which $Q^1$, $Q^2$, $R^1$, $R^2$, $R^3$ and $R^4$ have the meanings given above as being preferred.

Examples of compounds of the formula (I) which are very particularly preferred as active compound components according to the invention are listed in Table I below.

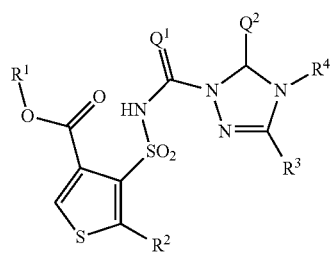

(I)

TABLE 1

| Examples of compounds of the formula (I) | | | | | | |
|---|---|---|---|---|---|---|
| Ex. No. | $Q^1$ | $Q^2$ | $R^1$ | $R^2$ | $R^3$ | $R^4$ | Melting point (° C.) |
| I-1 | O | O | $CH_3$ | $CH_3$ | $OC_2H_5$ | $CH_3$ | 163 |
| I-2 | O | O | $CH_3$ | $CH_3$ | $OCH_3$ | $CH_3$ | 201 |
| I-3 | O | O | $CH_3$ | $CH_3$ | $OC_3H_7$-n | $CH_3$ | 156 |
| I-4 | O | O | $CH_3$ | $CH_3$ | $OC_3H_7$-i | $CH_3$ | 150 |
| I-5 | O | O | $CH_3$ | $CH_3$ | $OCH_3$ | △ | 218 |
| I-6 | O | O | $CH_3$ | $CH_3$ | $OC_2H_5$ | △ | 170 |
| I-7 | O | O | $CH_3$ | $CH_3$ | $OC_3H_7$-n | △ | 156 |
| I-8 | O | O | $CH_3$ | $CH_3$ | $OC_3H_7$-i | △ | 188 |
| I-9 | O | O | $CH_3$ | $CH_3$ | △ | △ | 200 |
| I-10 | O | O | $CH_3$ | $CH_3$ | $CH_3$ | $CH_3$ | 178 |
| I-11 | O | O | $CH_3$ | $CH_3$ | $C_2H_5$ | $CH_3$ | 161 |
| I-12 | O | O | $CH_3$ | $CH_3$ | $SCH_3$ | $CH_3$ | 183 |
| I-13 | O | O | $C_2H_5$ | $CH_3$ | $OCH_3$ | $CH_3$ | 176 |
| I-14 | O | O | $CH_3$ | $CH_3$ | $CH_2OCH_3$ | △ | 185 |

TABLE 1-continued

| Examples of compounds of the formula (I) | | | | | | |
|---|---|---|---|---|---|---|
| Ex. No. | $Q^1$ | $Q^2$ | $R^1$ | $R^2$ | $R^3$ | $R^4$ | Melting point (° C.) |
| I-15 | O | O | $C_2H_5$ | $CH_3$ | $OC_2H_5$ | $CH_3$ | 172 |
| I-16 | O | O | $C_2H_5$ | $CH_3$ | $OCH_3$ | △ | 173 |
| I-17 | O | O | $CH_3$ | $CH_3$ | $C_2H_5$ | $OC_2H_5$ | 183 |
| I-18 | O | O | $CH_3$ | $CH_3$ | $C_2H_5$ | △ | 175 |

Very particular emphasis as active compound components according to the invention is also given to the sodium salts of the compounds from Table 1.

Preferred meanings of the groups listed above in connection with the compounds improving crop plant compatibility ("herbicide safeners") of the formulae (IIa), (IIb), (IIc), (IId) and (IIe) are defined below.

n preferably represents the numbers 0, 1, 2, 3 or 4.

$A^2$ preferably represents in each case optionally methyl-, ethyl-, methoxycarbonyl- or ethoxycarbonyl-substituted methylene or ethylene.

$R^5$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^6$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^7$ preferably represents in each case optionally fluorine-, chlorine- and/or bromine-substituted methyl, ethyl, n- or i-propyl.

$R^8$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl.

$R^9$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with $R^8$ represents one of the radicals —$CH_2$—O—$CH_2$—$CH_2$— and —$CH_2$—$CH_2$—O—$CH_2$—$CH_2$-, which are optionally substituted by methyl, ethyl, furyl, phenyl, a fused-on benzene ring or by two substituents which together with the C atom to which they are attached form a 5- or 6-membered carbocycle.

$R^{10}$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

$R^{11}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{12}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$R^{13}$ preferably represents hydrogen, methyl, ethyl, n- or i-propyl.

$R^{14}$ preferably represents hydrogen, methyl, ethyl, n- or i-propyl.

$R^{15}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

$R^{16}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{17}$ preferably represents hydrogen, represents in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl, ethyl, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{16}$ represents in each case optionally methyl- or ethyl-substituted butane-1,4-diyl (trimethylene), pentane-1,5-diyl, 1-oxa-butane-1,4-diyl or 3-oxa-pentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of compounds of the formula (IIa) which are very particularly preferred as herbicide safeners according to the invention are listed in Table 2 below.

TABLE 2

Examples of the compounds of the formula (IIa)

(IIa)

| Example No. | (positions) $(X^1)_n$ | $A^1$ | $R^5$ |
|---|---|---|---|
| IIa-1 | (2) Cl, (4) Cl | | $OCH_3$ |
| IIa-2 | (2) Cl, (4) Cl | | $OCH_3$ |
| IIa-3 | (2) Cl, (4) Cl | | $OC_2H_5$ |
| IIa-4 | (2) Cl, (4) Cl | | $OC_2H_5$ |
| IIa-5 | (2) Cl | | $OCH_3$ |

TABLE 2-continued

Examples of the compounds of the formula (IIa)

(IIa): (X¹)ₙ-phenyl(positions 2,3,4)-A¹-C(=O)-R⁵

| Example No. | (positions) (X¹)ₙ | A¹ | R⁵ |
|---|---|---|---|
| IIa-6 | (2) Cl, (4) Cl | 1-methyl-5-phenyl-pyrazol-3-yl (3-methyl) | OCH₃ |
| IIa-7 | (2) F | 1-methyl-5-phenyl-pyrazol-3-yl (3-methyl) | OCH₃ |
| IIa-8 | (2) F | 1-methyl-5-(2-chlorophenyl)-pyrazol-3-yl (3-methyl) | OCH₃ |
| IIa-9 | (2) Cl, (4) Cl | 1-methyl-3-trichloromethyl-1,2,4-triazol-5-yl (with methyl) | OC₂H₅ |
| IIa-10 | (2) Cl, (4) CF₃ | 1-methyl-3-phenyl-1,2,4-triazol-5-yl (with methyl) | OCH₃ |
| IIa-11 | (2) Cl | 1-methyl-3-(2-fluorophenyl)-1,2,4-triazol-5-yl (with methyl) | OCH₃ |
| IIa-12 | — | 3-methyl-5-phenyl-4,5-dihydroisoxazol-5-yl | OC₂H₅ |
| IIa-13 | (2) Cl, (4) Cl | 1-methyl-3-methyl-5-methyl-pyrazol-? (1-methyl-3,5-dimethyl-pyrazol-4-yl) | OC₂H₅ |
| IIa-14 | (2) Cl, (4) Cl | 1-methyl-3-methyl-5-isopropyl-pyrazol-4-yl | OC₂H₅ |
| IIa-15 | (2) Cl, (4) Cl | 1-methyl-3-methyl-5-tert-butyl-pyrazol-4-yl | OC₂H₅ |
| IIa-16 | (2) Cl, (4) Cl | (3-methyl-4,5-dihydroisoxazol-5-yl)-CH₂- | OC₂H₅ |
| IIa-17 | (2) Cl, (4) Cl | 3,5-dimethyl-4,5-dihydroisoxazol-5-yl | OC₂H₅ |

Examples of compounds of the formula (IIb) which are very particularly preferred as herbicide safeners according to the invention are listed in Table 3 below.

TABLE 3

Examples of compounds of the formula (IIb)

(IIb): 8-quinolinyl with X³ at position 5 (on ring carbons 3,4) and X² at position 5/6, with 8-O-A²-C(=O)-R⁶

| Example No. | (position) X² | (position) X³ | A² | R⁶ |
|---|---|---|---|---|
| IIb-1 | (5) Cl | — | CH₂ | OH |
| IIb-2 | (5) Cl | — | CH₂ | OCH₃ |
| IIb-3 | (5) Cl | — | CH₂ | OC₂H₅ |
| IIb-4 | (5) Cl | — | CH₂ | OC₃H₇-n |
| IIb-5 | (5) Cl | — | CH₂ | OC₃H₇-i |
| IIb-6 | (5) Cl | — | CH₂ | OC₄H₉-n |
| IIb-7 | (5) Cl | — | CH₂ | OCH(CH₃)C₅H₁₁-n |
| IIb-8 | (5) Cl | (2) F | CH₂ | OH |
| IIb-9 | (5) Cl | (2) Cl | CH₂ | OH |
| IIb-10 | (5) Cl | — | CH₂ | OCH₂CH=CH₂ |
| IIb-11 | (5) Cl | — | CH₂ | OC₄H₉-i |

TABLE 3-continued

Examples of compounds of the formula (IIb)

(IIb)

| Example No. | (position) X² | (position) X³ | A² | R⁶ |
|---|---|---|---|---|
| IIb-12 | (5) Cl | — | CH₂ | CH₂=CH-CH₂-O-CH₂-CH(OCH₃)-CH₃ (branched structure) |
| IIb-13 | (5) Cl | — | CH₂ with CH=CH₂ branch, O-C(=O)-CH(CH₃) | OCH₂CH=CH₂ |
| IIb-14 | (5) Cl | — | C₂H₅, O-C(=O)-CH(CH₃) | OC₂H₅ |

Examples of the compounds (IIc) which are very particularly preferred as herbicide safeners according to the invention are listed in Table 4 below.

TABLE 4

Examples of the compounds of the formula (IIc)

(IIc)

| Example No. | R⁷ | N(R⁸, R⁹) |
|---|---|---|
| IIc-1 | CHCl₂ | N(CH₂CH=CH₂)₂ |
| IIc-2 | CHCl₂ | 2,2-dimethyl-3-methyl-oxazolidine |
| IIc-3 | CHCl₂ | 2,2,3,5-tetramethyl-oxazolidine |
| IIc-4 | CHCl₂ | 3-methyl-1-oxa-4-aza-spiro[4.5]decane |
| IIc-5 | CHCl₂ | 2,2,3-trimethyl-5-phenyl-oxazolidine |
| IIc-6 | CHCl₂ | 3,4-dimethyl-3,4-dihydro-2H-benzo[1,4]oxazine |
| IIc-7 | CHCl₂ | 2,2,3-trimethyl-5-(furan-2-yl)-oxazolidine |

Examples of the compounds of the formula (IId) which are very particularly preferred as herbicide safeners according to the invention are listed in Table 5 below.

TABLE 5

Examples of the compounds of the formula (IId)

(IId)

| Example No. | $R^{13}$ | $R^{14}$ | $R^{15}$ | (positions) $(X^4)_n$ | (positions) $(X^5)_n$ |
| --- | --- | --- | --- | --- | --- |
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl(Me) | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2OCH_3$ | (2) $OCH_3$ | — |
| IId-26 | H | H | $CH_2OCH_3$ | (2) $OCH_3$ (5) $CH_3$ | — |

TABLE 6

Examples of the compounds of the formula (IIe)

(IIe)

| Example No. | $R^{13}$ | $R^{16}$ | $R^{17}$ | (positions) $(X^4)_n$ | (positions) $(X^5)_n$ |
| --- | --- | --- | --- | --- | --- |
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | H | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | cyclopropyl | (2) $OCH_3$ (5) $CH_3$ | — |
| IIe-12 | H | H | $CH_3$ | (2) $OCH_3$ (5) $CH_3$ | — |
| IIe-13 | H | H | $CH_2CH=CH_2$ | (2) $OCH_3$ | — |
| IIe-14 | H | H | $CH_2CH=CH_2$ | (2) $OCH_3$ (5) $CH_3$ | — |
| IIe-15 | H | H | $-CH_2-CH_2-O-CH_3$ | (2) $OCH_3$ | — |
| IIe-16 | H | H | $-CH_2-CH_2-O-CH_3$ | (2) $OCH_3$ (5) $CH_3$ | — |
| IIe-17 | H | H | $-CH_2-C\equiv CH$ | (2) $OCH_3$ | — |
| IIe-18 | H | H | $-CH_2-C\equiv CH$ | (2) $OCH_3$ (5) $CH_3$ | — |
| IIe-19 | H | H | $-CH_2-CH_2-O-C_2H_5$ | (2) $OCH_3$ | — |
| IIe-20 | H | H | $-CH_2-CH_2-O-C_2H_5$ | (2) $OCH_3$ (5) $CH_3$ | — |

Examples of the compounds of the formula (IIe) which are very particularly preferred as herbicide safeners according to the invention are listed in Table 6 below.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-22180974, DE-A-2350547).

The compounds of the general formula (IId) to be used as safeners according to the invention are known and/or can be prepared by processes known per se (cf. DE-A-19621522/ U.S. Pat. No. 6,235,680/WO 97/4016).

The compounds of the general formula (IIe) to be used as safeners according to the invention are known and/or can be prepared by processes known per se (cf. WO-A-99/66795/ U.S. Pat. No. 6,251,827).

Examples of the selectively herbicidal combinations according to the invention of in each case one active compound of the formula (I) and in each case one of the safeners defined above are listed in Table 7 below.

TABLE 7

Examples of combinations according to the invention

| Active compound of the formula (I) | Safener |
|---|---|
| I-1 | AD-67 |
| I-1 | cloquintocet-mexyl |
| I-1 | dichlormid |
| I-1 | fenchlorazole-ethyl |
| I-1 | isoxadifen-ethyl |
| I-1 | mefenpyr-diethyl |
| I-1 | MON-7400 |
| I-1 | flurazole |
| I-1 | furilazole |
| I-1 | fenclorim |
| I-1 | cumyluron |
| I-1 | daimuron/dymron |
| I-1 | dimepiperate |
| I-1 | IId-25 |
| I-1 | IIe-11 |
| I-2 | AD-67 |
| I-2 | cloquintocet-mexyl |
| I-2 | dichlormid |
| I-2 | fenchlorazole-ethyl |
| I-2 | isoxadifen-ethyl |
| I-2 | mefenpyr-diethyl |
| I-2 | MON-7400 |
| I-2 | flurazole |
| I-2 | furilazole |
| I-2 | fenclorim |
| I-2 | cumyluron |
| I-2 | daimuron/dymron |
| I-2 | dimepiperate |
| I-2 | IId-25 |
| I-2 | IIe-11 |
| I-3 | AD-67 |
| I-3 | cloquintocet-mexyl |
| I-3 | dichlormid |
| I-3 | fenchlorazole-ethyl |
| I-3 | isoxadifen-ethyl |
| I-3 | mefenpyr-diethyl |
| I-3 | MON-7400 |
| I-3 | flurazole |
| I-3 | furilazole |
| I-3 | fenclorim |
| I-3 | cumyluron |
| I-3 | daimuron/dymron |
| I-3 | dimepiperate |
| I-3 | IId-25 |
| I-3 | IIe-11 |
| I-4 | AD-67 |
| I-4 | cloquintocet-mexyl |
| I-4 | dichlormid |
| I-4 | fenchlorazole-ethyl |
| I-4 | isoxadifen-ethyl |
| I-4 | mefenpyr-diethyl |

TABLE 7-continued

Examples of combinations according to the invention

| Active compound of the formula (I) | Safener |
|---|---|
| I-4 | MON-7400 |
| I-4 | flurazole |
| I-4 | furilazole |
| I-4 | fenclorim |
| I-4 | cumyluron |
| I-4 | daimuron/dymron |
| I-4 | dimepiperate |
| I-4 | IId-25 |
| I-4 | IIe-11 |
| I-5 | AD-67 |
| I-5 | cloquintocet-mexyl |
| I-5 | dichlormid |
| I-5 | fenchlorazole-ethyl |
| I-5 | isoxadifen-ethyl |
| I-5 | mefenpyr-diethyl |
| I-5 | MON-7400 |
| I-5 | flurazole |
| I-5 | furilazole |
| I-5 | fenclorim |
| I-5 | cumyluron |
| I-5 | daimuron/dymron |
| I-5 | dimepiperate |
| I-5 | IId-25 |
| I-5 | IIe-11 |
| I-6 | AD-67 |
| I-6 | cloquintocet-mexyl |
| I-6 | dichlormid |
| I-6 | fenchlorazole-ethyl |
| I-6 | isoxadifen-ethyl |
| I-6 | mefenpyr-diethyl |
| I-6 | MON-7400 |
| I-6 | flurazole |
| I-6 | furilazole |
| I-6 | fenclorim |
| I-6 | cumyluron |
| I-6 | daimuron/dymron |
| I-6 | dimepiperate |
| I-6 | IId-25 |
| I-6 | IIe-11 |
| I-7 | AD-67 |
| I-7 | cloquintocet-mexyl |
| I-7 | dichlormid |
| I-7 | fenchlorazole-ethyl |
| I-7 | isoxadifen-ethyl |
| I-7 | mefenpyr-diethyl |
| I-7 | MON-7400 |
| I-7 | flurazole |
| I-7 | furilazole |
| I-7 | fenclorim |
| I-7 | cumyluron |
| I-7 | daimuron/dymron |
| I-7 | dimepiperate |
| I-7 | IId-25 |
| I-7 | IIe-11 |
| I-8 | AD-67 |
| I-8 | cloquintocet-mexyl |
| I-8 | dichlormid |
| I-8 | fenchlorazole-ethyl |
| I-8 | isoxadifen-ethyl |
| I-8 | mefenpyr-diethyl |
| I-8 | MON-7400 |
| I-8 | flurazole |
| I-8 | furilazole |
| I-8 | fenclorim |
| I-8 | cumyluron |
| I-8 | daimuron/dymron |
| I-8 | dimepiperate |
| I-8 | IId-25 |
| I-8 | IIe-11 |
| I-9 | AD-67 |
| I-9 | cloquintocet-mexyl |
| I-9 | dichlormid |
| I-9 | fenchlorazole-ethyl |
| I-9 | isoxadifen-ethyl |
| I-9 | mefenpyr-diethyl |
| I-9 | MON-7400 |

TABLE 7-continued

Examples of combinations according to the invention

| Active compound of the formula (I) | Safener |
|---|---|
| I-9 | flurazole |
| I-9 | furilazole |
| I-9 | fenclorim |
| I-9 | cumyluron |
| I-9 | daimuron/dymron |
| I-9 | dimepiperate |
| I-9 | IId-25 |
| I-9 | IIe-11 |
| I-10 | AD-67 |
| I-10 | Cloquintocet-mexyl |
| I-10 | dichlormid |
| I-10 | fenchlorazole-ethyl |
| I-10 | isoxadifen-ethyl |
| I-10 | mefenpyr-diethyl |
| I-10 | MON-7400 |
| I-10 | flurazole |
| I-10 | furilazole |
| I-10 | fenclorim |
| I-10 | cumyluron |
| I-10 | daimuron/dymron |
| I-10 | dimepiperate |
| I-10 | IId-25 |
| I-10 | IIe-11 |
| I-11 | AD-67 |
| I-11 | cloquintocet-mexyl |
| I-11 | dichlormid |
| I-11 | fenchlorazole-ethyl |
| I-11 | isoxadifen-ethyl |
| I-11 | mefenpyr-diethyl |
| I-11 | MON-7400 |
| I-11 | flurazole |
| I-11 | furilazole |
| I-11 | fenclorim |
| I-11 | cumyluron |
| I-11 | daimuron/dymron |
| I-11 | dimepiperate |
| I-11 | IId-25 |
| I-11 | IIe-11 |
| I-12 | AD-67 |
| I-12 | cloquintocet-mexyl |
| I-12 | dichlormid |
| I-12 | fenchlorazole-ethyl |
| I-12 | isoxadifen-ethyl |
| I-12 | mefenpyr-diethyl |
| I-12 | MON-7400 |
| I-12 | flurazole |
| I-12 | furilazole |
| I-12 | fenclorim |
| I-12 | cumyluron |
| I-12 | daimuron/dymron |
| I-12 | dimepiperate |
| I-12 | IId-25 |
| I-12 | IIe-11 |
| I-13 | mefenpyr-diethyl |
| I-2, sodium salt | IId-25 |
| I-15 | mefenpyr-diethyl |
| I-16 | mefenpyr-diethyl |
| I-17 | mefenpyr-diethyl |
| I-14 | mefenpyr-diethyl |
| I-18 | mefenpyr-diethyl |

Surprisingly, it has now been found that the above-defined active compound combinations of substituted thien-3-ylsulphonylamino(thio)carbonyltriazolin(ethi)ones of the general formula (I) and/or their salts and safeners (antidotes) of group (2) listed above, whilst being tolerated very well by crop plants, have particularly high herbicidal activity and can be used in various crops, in particular in cereal (especially wheat) and maize, but also in soya beans, potatoes and rice, for the selective control of weeds.

Here, it has to be considered to be surprising that, from a large number of known safeners or antidotes which are capable of antagonizing the damaging effect of a herbicide on the crop plants, that are in particular the abovementioned compounds of group (2) which neutralize the damaging effect of substituted thien-3-ylsulphonylamino(thio)carbonyltriazolin(ethi)ones on the crop plants virtually completely without negatively affecting the herbicidal activity with respect to the weeds.

Emphasis is given here to the particularly advantageous effect of the particularly and most preferred combination partners from group (2), in particular in respect of sparing cereal plants, such as, for example, wheat, barley and rye, but also maize and rice, as crop plants.

The active compound combinations according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Monocotyledonous crops of the genera: *Oryza, Zea, Triticum, Hordeum, Avena, Secale, Sorghum, Panicum, Saccharum, Ananas, Asparagus, Allium.*

However, the use of the active compound combinations according to the invention is in no way restricted to these genera, but also extends in the same manner to other plants. According to the invention, crop plants are all plants and plant varieties including transgenic plants and plant varieties, where on transgenic plants and plant varieties it is also possible for synergistic effects to occur.

The advantageous effect of the crop plant compatibility of the active compound combinations according to the invention is particularly highly pronounced at certain concentration ratios. However, the weight ratios of the active compounds in the active compound concentrations can be varied within relatively wide ranges. In general, 0.001 to 1000 parts by weight, preferably 0.01 to 100 parts by weight, and particularly preferably 0.1 to 50 parts by weight and most preferably 1 to 25 parts by weight of one of the compounds which improve crop plant compatibility mentioned under group 2 above (antidotes/safeners) are present per part by weight of active compound of the formula (I) or its salts.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethy) sulphoxide, and also water.

Suitable solid carriers are:
for example ammonium salts and ground natural minerals, such as kaolins, clays, talc, chalk, quartz, attapulgite, montmorillonite or diatomaceous earth, ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise from 0.1 to 95 percent by weight of active compounds including the safeners, preferably between 0.5 and 90%.

The active compound combinations according to the invention are generally used in the form of finished formulations. However, the active compounds contained in the active compound combinations can also be mixed in individual formulations when used, i.e. in the form of tank mixes.

The novel active compound combinations, as such or in their formulations, can furthermore be used as a mixture with other known herbicides, finished formulations or tank mixes again being possible. A mixture with other known active compounds, such as fungicides, insecticides, acaricides, nematicides, bird repellents, growth factors, plant nutrients and agents which improve soil structure, is also possible. For certain intended uses, in particular in the post-emergence method, it may furthermore be advantageous to include, as further additives in the formulations, mineral or vegetable oils which are tolerated by plants (for example the commercial preparation "Rako Binol"), or ammonium salts such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. They are used in the customary manner, for example by washing, spraying, atomizing, dusting or scattering.

The amounts of the active compound combinations according to the invention applied can be varied within a certain range; they depend, inter alia, on the weather and on soil factors. In general, the application rates are between 0.001 and 5 kg per ha, preferably between 0.001 and 1 kg per ha, particularly preferably between 0.003 and 0.5 kg per ha.

The active compound combinations according to the invention can be applied before and after emergence of the plants, that is to say by the pre-emergence and post-emergence method.

USE EXAMPLES

The active compound or safener components are in each case dissolved in a few ml (generally 2-3 ml) of solvent (generally acetone or N,N-dimethyl-formamide), and the solutions are combined and then—if appropriate after addition of an emulsifier—diluted with water to the desired concentration. In general, an aqueous spray liquor was prepared using 0.1% of the additive Renex-36.

Example A

Post-Emergence Test

The test plants are grown under controlled conditions (temperature, light, atmospheric humidity) in a greenhouse. The test plants are sprayed when they have reached a height of 5-15 cm. The concentration of the spray liquor is chosen such that the particular amounts of active compound desired are applied in 500l of water/ha.

After spraying, the pots with the test plants are kept in a greenhouse chamber under controlled conditions (temperature, light, atmospheric humidity) until the test has ended. About three weeks after the application, the degree of damage to the crop plants is rated in % damage in comparison to the development of the untreated control.

The figures denote:
0%=no damage (like untreated control)
100%=total destruction/damage Active compounds, application rates, test plants and results are shown in the tables below, the terms being used in the tables being as defined below:
maize=maize cv. "Pioneer"
a.i.=active ingredient=active compound/safener

TABLE A1

Post-emergence test/greenhouse

| Active compound (+safener) | Application rate (g of a.i./ha) | Damage maize (in %) |
|---|---|---|
| I-2 | 10 | 35 |
| I-2 + AD-67 | 10 + 100 | 7 |
| I-2 + cloquintocet-mexyl | 10 + 100 | 1.5 |
| I-2 + dichlormid | 10 + 100 | 13.5 |
| I-2 + fenchlorazole-ethyl | 10 + 100 | 12 |
| I-2 + isoxadifen-ethyl | 10 + 100 | 4 |
| I-2 + furilazole | 10 + 100 | 2.5 |
| I-2 + flurazole | 10 + 100 | 4.5 |
| I-2 + IIe-11 | 10 + 100 | 2 |
| I-2 + MON-7400 | 10 + 100 | 1.5 |

Example A-2

Post-Emergence Test

Here, an aqueous spray liquor comprising 0.5% of the additive Renex-36 was prepared.

Ex. No. 1-2, sodium salt =

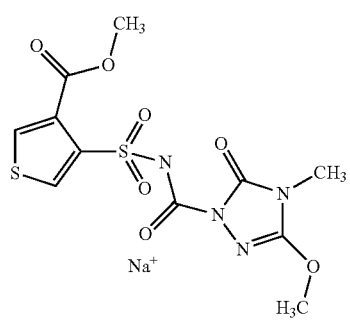

Ex.-No. IId-25 =

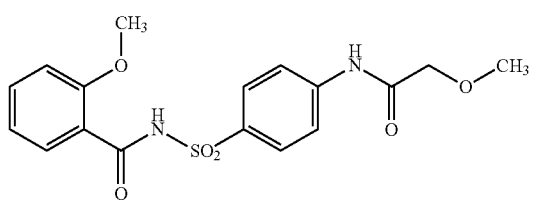

TABLE A-2

Post-emergence test/greenhouse

| Active compound (+safener) | Application rate (g of a.i./ha) | Damage winter barley (in %) |
|---|---|---|
| I-2, sodium salt | 4 | 60 |
|  | 2 | 50 |
| I-2, sodium salt + Comp. No. IId-25 | 4 + 100 | 50 |
|  | 2 + 100 | 25 |
|  | 4 + 30 | 50 |
|  | 2 + 30 | 35 |
| Safener |  |  |
| Comp. No. IId-25 | 100 | 0 |
|  | 30 | 0 |

Example A-3

Post-Emergence Test

The compound I-2 was used as 10 WP. In each case, Marlipal® was added in an amount of 500 ml/ha.

Evaluation was carried out as early as 7 days after the application.

Maize 1=maize of the cultivar "Prinz"
Maize 2=maize of the cultivar "Pioneer"
Maize 3=maize of the cultivar "LIXIS"

TABLE A-3

Post-emergence test/greenhouse

| Active compound (+safener) | Application rate (g of a.i./ha) | Damage maize 1 (in %) |
|---|---|---|
| I-2 | 15 | 20 |
|  | 8 | 10 |
| I-2 + Comp. No. IId-25 | 15 + 100 | 5 |
|  | 8 + 100 | 0 |

| Active compound (+safener) | Application rate (g of a.i./ha) | Damage maize 2 (in %) |
|---|---|---|
| I-2 | 15 | 20 |
|  | 8 | 10 |
| I-2 + Comp. No. IId-25 | 15 + 100 | 5 |
|  | 8 + 100 | 5 |

| Active compound (+safener) | Application rate (g of a.i./ha) | Damage Maize 3 (in %) |
|---|---|---|
| I-2 | 15 | 40 |
|  | 8 | 20 |
| I-2 + Comp. No. IId-25 | 15 + 100 | 20 |
|  | 8 + 100 | 10 |
|  | 15 + 50 | 10 |
|  | 8 + 50 | 10 |

Example A-4

Post-Emergence Test

Mefenpyr-diethyl was used as 100 EC.
The compounds of Ex. Nos. I-2 and I-13 were used as 10 WP.

TABLE A-4

Post-emergence test/greenhouse

| Safener | Application rate (g of a.i./ha) | Damage winter wheat (in %) |
|---|---|---|
| mefenpyr-diethyl | 50 | 0 |

| Active compound (+safener) | Application rate (g of a.i./ha) | Damage winter wheat (in %) |
|---|---|---|
| I-2 | 30 | 60 |
|  | 15 | 40 |
| I-2 + mefenpyr-diethyl | 30 + 50 | 10 |
|  | 15 + 50 | 5 |

| Active compound (+safener) | Application rate (g of a.i./ha) | Damage winter wheat (in %) |
|---|---|---|
| I-13 | 125 | 30 |
|  | 60 | 20 |
| I-13 + mefenpyr-diethyl | 125 + 50 | 10 |
|  | 60 + 50 | 5 |

| Safener | Application rate (g of a.i./ha) | Damage winter wheat (in %) |
|---|---|---|
| mefenpyr-diethyl | 50 | 0 |

| Active compound (+safener) | Application rate (g of a.i./ha) | Damage winter barley (in %) |
|---|---|---|
| I-2 | 30 | 80 |
|  | 15 | 70 |
|  | 8 | 50 |

TABLE A-4-continued

Post-emergence test/greenhouse

| Active compound (+safener) | Application rate (g of a.i./ha) | Damage winter barley (in %) |
|---|---|---|
| I-2 + mefenpyr-diethyl | 30 + 50 | 70 |
|  | 15 + 50 | 40 |
|  | 8 + 50 | 30 |

| Active compound (+safener) | Application rate (g of a.i./ha) | Damage winter barley (in %) |
|---|---|---|
| I-13 | 125 | 80 |
|  | 60 | 70 |
|  | 30 | 50 |
| I-13 + mefenpyr-diethyl | 125 + 50 | 60 |
|  | 60 + 50 | 50 |
|  | 30 + 50 | 30 |

Example A-5

Post-Emergence Test

Mefenpyr-diethyl was used as 100 EC and the compound of Ex. No. I-2 was used as 10 WP.

TABLE A-5

Post-emergence test/greenhouse

| Active compound (+safener) | Application rate (g of a.i./ha) | Damage winter wheat (in %) |
|---|---|---|
| I-2 | 30 | 60 |
| mefenpyr-diethyl | 50 | 0 |
| I-2 + mefenpyr-diethyl | 30 + 50 | 5 |

| Active compound (+safener) | Application rate (g of a.i./ha) | Damage winter wheat (in %) |
|---|---|---|
| I-13 | 125 | 50 |
| mefenpyr-diethyl | 50 | 0 |
| I-13 + mefenpyr-diethyl | 125 + 50 | 10 |

| Active compound (+safener) | Application rate (g of a.i./ha) | Damage winter wheat (in %) |
|---|---|---|
| I-15 | 60 | 80 |
| mefenpyr-diethyl | 50 | 0 |
| I-15 + mefenpyr-diethyl | 60 + 50 | 40 |

| Active compound (+safener) | Application rate (g of a.i./ha) | Damage winter wheat (in %) |
|---|---|---|
| I-16 | 60 | 25 |
| mefenpyr-diethyl | 50 | 0 |
| I-60 + mefenpyr-diethyl | 60 + 50 | 15 |

| Safener | Application rate (g of a.i./ha) | Damage winter wheat (in %) |
|---|---|---|
| mefenpyr-diethyl | 50 | 0 |

| Active compound (+safener) | Application rate (g of a.i./ha) | Damage winter wheat (in %) |
|---|---|---|
| I-2 | 30 | 40 |
|  | 15 | 30 |
|  | 8 | 20 |

TABLE A-5-continued

Post-emergence test/greenhouse

| Active compound (+safener) | Application rate (g of a.i./ha) | Damage winter wheat (in %) |
|---|---|---|
| I-2 + mefenpyr-diethyl | 30 + 50 | 20 |
|  | 15 + 50 | 10 |
|  | 8 + 50 | 10 |

| Active compound (+safener) | Application rate (g of a.i./ha) | Damage winter wheat (in %) |
|---|---|---|
| I-17 | 30 | 70 |
|  | 15 | 50 |
|  | 8 | 40 |
| I-17 + mefenpyr-diethyl | 30 + 50 | 40 |
|  | 15 + 50 | 30 |
|  | 8 + 50 | 20 |

| Active compound (+safener) | Application rate (g of a.i./ha) | Damage winter wheat (in %) |
|---|---|---|
| I-14 | 1 | 40 |
|  | 0.5 | 20 |
| I-14 + mefenpyr-diethyl | 1 + 50 | 30 |
|  | 0.5 + 50 | 10 |

| Active compound (+safener) | Application rate (g of a.i./ha) | Damage winter wheat (in %) |
|---|---|---|
| I-18 | 2 | 50 |
|  | 1 | 30 |
| I-18 + mefenpyr-diethyl | 2 + 50 | 20 |
|  | 1 + 50 | 10 |

| Active compound (+safener) | Application rate (g of a.i./ha) | Damage winter wheat (in %) |
|---|---|---|
| I-15 | 30 | 70 |
|  | 15 | 40 |
|  | 8 | 30 |
| I-15 + mefenpyr-diethyl | 30 + 50 | 10 |
|  | 15 + 50 | 0 |
|  | 8 + 50 | 0 |

| Safener | Application rate (g of a.i./ha) | Damage winter barley (in %) |
|---|---|---|
| mefenpyr-diethyl | 50 | 0 |

| Active compound (+safener) | Application rate (g of a.i./ha) | Damage winter barley (in %) |
|---|---|---|
| I-2 | 30 | 80 |
|  | 15 | 70 |
|  | 8 | 60 |
| I-2 + mefenpyr-diethyl | 30 + 50 | 50 |
|  | 15 + 50 | 20 |
|  | 8 + 50 | 10 |

| Active compound (+safener) | Application rate (g of a.i./ha) | Damage winter barley (in %) |
|---|---|---|
| I-17 | 30 | 80 |
|  | 15 | 70 |
|  | 8 | 70 |
| I-17 + mefenpyr-diethyl | 30 + 50 | 70 |
|  | 15 + 50 | 60 |
|  | 8 + 50 | 20 |

| Active compound (+safener) | Application rate (g of a.i./ha) | Damage winter barley (in %) |
|---|---|---|
| I-14 | 0.5 | 30 |
|  | 0.25 | 10 |

TABLE A-5-continued

Post-emergence test/greenhouse

| Active compound (+safener) | Application rate (g of a.i./ha) | Damage winter barley (in %) |
|---|---|---|
| I-14 + mefenpyr-diethyl | 0.5 + 50 | 20 |
|  | 0.25 + 50 | 0 |

| Active compound (+safener) | Application rate (g of a.i./ha) | Damage winter barley (in %) |
|---|---|---|
| I-18 | 2 | 60 |
|  | 1 | 20 |
|  | 0.5 | 10 |
| I-18 + mefenpyr-diethyl | 2 + 50 | 20 |
|  | 1 + 50 | 10 |
|  | 0.5 + 50 | 0 |

| Active compound (+safener) | Application rate (g of a.i./ha) | Damage winter barley (in %) |
|---|---|---|
| I-15 | 30 | 80 |
|  | 15 | 70 |
|  | 8 | 60 |
| I-15 + mefenpyr-diethyl | 30 + 50 | 30 |
|  | 15 + 50 | 20 |
|  | 8 + 50 | 10 |

The invention claimed is:

1. A composition comprising an active compound combination comprising (a) a compound of formula (I)

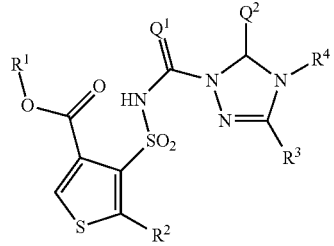

or salts thereof, in which $Q^1$, $Q^2$, $R^1$, $R^2$, $R^3$, $R^4$ are defined as follows

| Ex. No. | $Q^1$ | $Q^2$ | $R^1$ | $R^2$ | $R^3$ | $R^4$ |
|---|---|---|---|---|---|---|
| I-2 | O | O | $CH_3$ | $CH_3$ | $OCH_3$ | $CH_3$ | and (b) a crop-plant-compatibility-improving compound of formula (IIe)

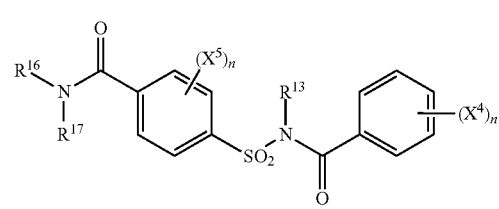

wherein
$R^{13}$ and $R^{16}$ each represent hydrogen, $R^{17}$ represents cyclopropyl, $(X^4)_n$ represents 2-methoxy, and $(X^5)_n$ represents hydrogen.

2. A composition of claim 1, wherein the ratio of said at least one compound that improves crop plant compatibility per part by weight of said compound of formula I or a salt thereof is from 0.1 to 50.

3. A process for preparing a herbicidal composition comprising mixing a composition according to claim 1, with one or more surfactants and/or extenders.

4. A method for controlling undesirable plants comprising allowing an effective amount of a composition according to claim 1, to act on undesirable plants and/or their habitat.

5. A method according to claim 4, wherein the undesired plants are controlled in areas of growing maize.

6. A method according to claim 5, wherein 0.001 to 5 kg per ha of the composition are applied.

7. A method according to claim 5, wherein 0.001 to 1 kg per ha of the composition are applied.

8. A method according to claim 5, wherein 0.003 to 0.5 kg per ha of the composition are applied.

9. A method according to claim 5, wherein the composition is applied pre-emergence.

10. A method according to claim 5, wherein the composition is applied post-emergence.

* * * * *